United States Patent
Ioka et al.

(10) Patent No.: US 10,835,104 B2
(45) Date of Patent: Nov. 17, 2020

(54) IMAGE PROCESSING DEVICE, ENDOSCOPE SYSTEM, IMAGE PROCESSING METHOD, AND PROGRAM

(71) Applicant: OLYMPUS CORPORATION, Hachioji (JP)

(72) Inventors: Ken Ioka, Hachioji (JP); Kazunori Yoshizaki, Hachioji (JP); Sunao Kikuchi, Akiruno (JP); Yasuhiro Komiya, Sagamihara (JP); Yasuhiro Fukunaga, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 654 days.

(21) Appl. No.: 15/666,562

(22) Filed: Aug. 1, 2017

(65) Prior Publication Data
US 2017/0325658 A1    Nov. 16, 2017

Related U.S. Application Data

(63) Continuation of application No. PCT/JP2015/053687, filed on Feb. 10, 2015.

(51) Int. Cl.
*G06K 9/36* (2006.01)
*A61B 1/00* (2006.01)
(Continued)

(52) U.S. Cl.
CPC ...... *A61B 1/00009* (2013.01); *A61B 1/00186* (2013.01); *A61B 1/051* (2013.01);
(Continued)

(58) Field of Classification Search
CPC ... A61B 1/00009; A61B 1/0646; A61B 1/051; A61B 1/0638; A61B 1/00186
See application file for complete search history.

(56) References Cited

U.S. PATENT DOCUMENTS 7,466,451 B2 * 12/2008 Kobayashi ............ H04N 5/772
                                                          358/1.9
7,548,264 B2 *  6/2009 Mitsunaga ............ H04N 9/045
                                                          348/272
(Continued)

FOREIGN PATENT DOCUMENTS

CN    102201114 A    9/2011
CN    102458215 A    5/2012
(Continued)

OTHER PUBLICATIONS

International Search Report (ISR) and Written Opinion dated Apr. 28, 2015 issued in International Application No. PCT/JP2015/053687.

(Continued)

*Primary Examiner* — Amir Alavi
(74) *Attorney, Agent, or Firm* — Holtz, Holtz & Volek PC

(57) ABSTRACT

An image processing device includes: a separation unit configured to separate a plurality of wide-band image signals corresponding to wide-band light passing through each of a plurality of wide-band filters and a narrow-band image signal corresponding to narrow-band light passing through a narrow-band filter, from each other, based on an image signal input from an imaging device; a demosaicing unit configured to perform demosaic processing that interpolates one of the plurality of wide-band image signals based on edge information from the narrow-band image signal separated by the separation unit; and an image generation unit configured to generate a wide-band image by using the wide-band image signal interpolated by the demosaic processing performed by the demosaicing unit and generate a narrow-band image by using the narrow-band image signal.

20 Claims, 12 Drawing Sheets

(51) Int. Cl.
  *G06T 3/40*  (2006.01)
  *A61B 1/05*  (2006.01)
  *A61B 1/06*  (2006.01)

(52) U.S. Cl.
  CPC .......... *A61B 1/0638* (2013.01); *A61B 1/0646* (2013.01); *G06T 3/4015* (2013.01)

(56) References Cited

U.S. PATENT DOCUMENTS

| | | | |
|---|---|---|---|
| 7,653,240 B1* | 1/2010 | Otobe | G06T 3/4015 382/162 |
| 8,390,679 B2 | 3/2013 | Uchiyama et al. | |
| 8,500,632 B2 | 8/2013 | Gono | |
| 8,599,291 B2* | 12/2013 | Min | H04N 5/332 348/273 |
| 9,095,269 B2 | 8/2015 | Morita | |
| 9,258,549 B2* | 2/2016 | DiCarlo | A61B 1/00193 |
| 9,629,525 B2 | 4/2017 | Morita | |
| 9,659,346 B2* | 5/2017 | Nakamura | G06T 3/4007 |
| 9,681,109 B2* | 6/2017 | Siddiqui | G02B 5/201 |
| 9,990,695 B2* | 6/2018 | Nishimura | G06T 11/001 |
| 10,321,816 B2* | 6/2019 | Morimoto | A61B 1/0638 |
| 10,362,930 B2* | 7/2019 | Sasaki | H04N 9/045 |
| 2011/0235877 A1 | 9/2011 | Morita | |
| 2011/0273548 A1 | 11/2011 | Uchiyama et al. | |
| 2015/0305607 A1 | 10/2015 | Morita | |
| 2017/0325658 A1* | 11/2017 | Ioka | A61B 1/00186 |

FOREIGN PATENT DOCUMENTS

| | | |
|---|---|---|
| JP | 2007020880 A | 2/2007 |
| JP | 2014103597 A | 6/2014 |
| WO | 2010143692 A1 | 12/2010 |

OTHER PUBLICATIONS

Daisuke Kiku et al., "Simultaneous Capturing of RGB and Additional Band Images Using Hybrid Color Filter Array," Proc. of SPIE-IS&T, vol. 9023, pp. 90230V-1 to 90230V-9.

Chinese Office Action dated Jul. 3, 2018 (and English translation thereof) issued in counterpart Chinese Application No. 201580075786.6.

* cited by examiner

IMAGE PROCESSING DEVICE, ENDOSCOPE SYSTEM, IMAGE PROCESSING METHOD, AND PROGRAM

CROSS REFERENCES TO RELATED APPLICATIONS

This application is a continuation of International Application No. PCT/JP2015/053687, filed on Feb. 10, 2015, the entire contents of which are incorporated herein by reference.

BACKGROUND

The present disclosure relates to an image processing device, an endoscope system, an imaging device, an image processing method, and a program.

In recent years, in the field of endoscope, a technique is known which simultaneously acquires a narrow-band image, where capillary vessels and a mucosal fine pattern of a mucosal surface layer may be observed, and a normal wide-band image by providing a color filter, where a plurality of wide-band filters that transmits wide-band light in a visible region and a plurality of narrow-band filters that transmits narrow-band light are arranged in a two-dimensional matrix form, in a light receiving surface of an imaging sensor (see JP 2007-20880 A).

SUMMARY

An image processing device according to one aspect of the present disclosure includes: a separation unit configured to separate a plurality of wide-band image signals corresponding to wide-band light passing through each of a plurality of wide-band filters and a narrow-band image signal corresponding to narrow-band light passing through a narrow-band filter, from each other, based on an image signal input from an imaging device, the imaging device including: an imaging sensor that generates the image signal by photoelectrically converting light received by each of a plurality of pixels arranged in a two-dimensional lattice shape; and a color filter formed of the plurality of wide-band filters that transmit the wide-band light including primary color wavelength bands different from each other and the narrow-band filter that has a wavelength band narrower than a wavelength band of the wide-band light transmitted by each of the plurality of wide-band filters and transmits the narrow-band light included in a part of the wavelength bands of the wide-band light, number of filters of the narrow-band filter being greater than or equal to number of filters of any one of the plurality of wide-band filters, the color filter being arranged corresponding to each of the plurality of pixels; a demosaicing unit configured to perform demosaic processing that interpolates one of the plurality of wide-band image signals based on edge information from the narrow-band image signal separated by the separation unit; and an image generation unit configured to generate a wide-band image by using the wide-band image signal interpolated by the demosaic processing performed by the demosaicing unit and generate a narrow-band image by using the narrow-band image signal.

The above and other features, advantages and technical and industrial significance of this disclosure will be better understood by reading the following detailed description of presently preferred embodiments of the disclosure, when considered in connection with the accompanying drawings.

DETAILED DESCRIPTION

Hereinafter, modes for carrying out the present disclosure (hereinafter referred to as "embodiments") will be described. In the embodiments, a medical endoscope system, which functions as an image processing device and captures and displays images in a body cavity of a subject such as a patient, will be described as an example. The present disclosure is not limited by the embodiments described below. In the description of the drawings, the same components are denoted by the same reference symbols.

First Embodiment

Configuration of Endoscope System

Figure 1:
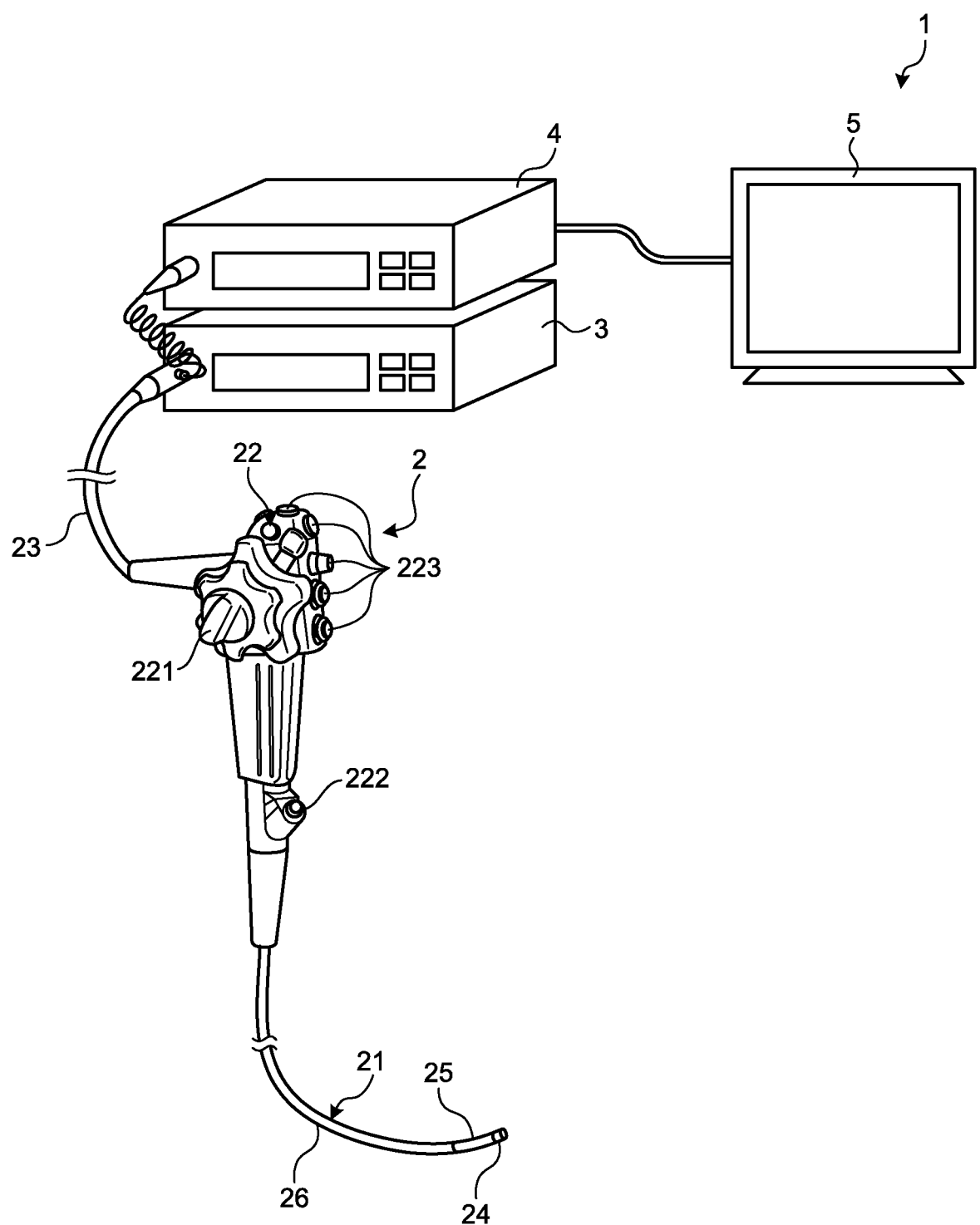
FIG. 1 is a diagram illustrating a schematic configuration of an endoscope system according to a first embodiment of the present disclosure.
Figure 2:
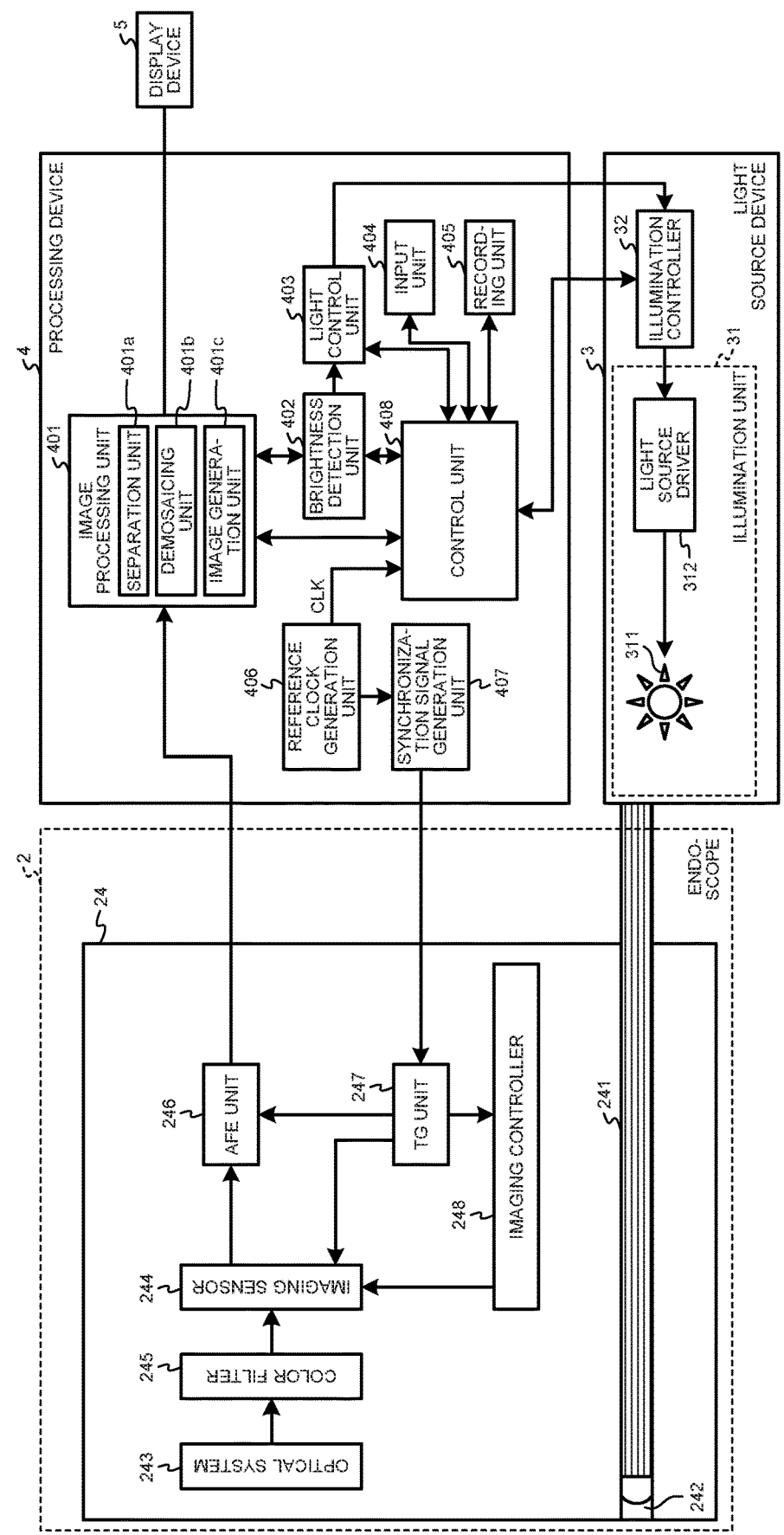
FIG. 2 is a block diagram illustrating a functional configuration of essential parts of the endoscope system according to the first embodiment of the present disclosure.

FIG. 1 is a diagram illustrating a schematic configuration of an endoscope system according to a first embodiment of the present disclosure. FIG. 2 is a block diagram illustrating a functional configuration of essential parts of the endoscope system according to the first embodiment of the present disclosure.

An endoscope system 1 illustrated in FIGS. 1 and 2 includes an endoscope 2 that captures in-vivo images of a subject when the distal end portion of the endoscope 2 is inserted into a body cavity of the subject, a light source device 3 that generates illumination light to be emitted from the distal end of the endoscope 2, a processing device 4 (processor) that generates an image by performing predetermined image processing on an image signal captured by the endoscope 2 and integrally controls the entire operation of the endoscope system 1, and a display device 5 that displays the image generated by the processing device 4 that has performed the image processing.

Configuration of Endoscope

First, a configuration of the endoscope 2 will be described. The endoscope 2 includes an insertion portion 21 having a flexible elongated shape, an operating unit 22 that is connected to the proximal end of the insertion portion 21 and receives inputs of various operation signals, and a universal cord 23 that extends in a direction different from a direction in which the insertion portion 21 extends from the operating unit 22 and incorporates various cables that connect to the light source device 3 and the processing device 4.

The insertion portion 21 includes a distal end portion 24 incorporating an imaging sensor 244 (imaging device) in which pixels that generate signals by receiving light and performing photoelectric conversion are two-dimensionally arranged, a bendable bending portion 25 including a plurality of bending pieces, and a flexible tube portion 26 which has a long and flexible shape and is connected to the proximal end of the bending portion 25.

The distal end portion 24 includes a light guide 241, an illumination lens 242, an optical system 243, a color filter 245, the imaging sensor 244, an analog front end unit 246 (hereinafter referred to as an "AFE unit 246"), a timing generator unit 247 (hereinafter referred to as a "TG unit 247"), and an imaging controller 248.

The light guide 241 is formed by using glass fiber and the like and forms a light guide path of the light emitted by the light source device 3. The illumination lens 242 is provided at the distal end of the light guide 241 and emits light guided by the light guide 241 to an object.

The optical system 243 is configured by using one or a plurality of lenses, a prism, and the like and has an optical zoom function that changes an angle of view and a focus function that changes a focal point.

The imaging sensor 244 generates an electrical signal by receiving light having passed through the optical system 243 and the color filter 245 and performing photoelectric conversion, and outputs the electrical signal as an image signal. The imaging sensor 244 is formed by using an imaging sensor such as a CCD (Charge Coupled Device) or a CMOS (Complementary Metal Oxide Semiconductor) where a plurality of pixels that receives light from the optical system 243 is arranged in a two-dimensional matrix form. The imaging sensor 244 generates an image signal according to a signal input from the TG unit 247 and a clock signal input from the processing device 4 under control of the imaging controller 248.

The color filter 245 is provided by being laminated on a light receiving surface of the imaging sensor 244. The color filter 245 is formed by arranging filter units. Each of the filter units is formed by using a plurality of wide-band filters that transmits wide-band light including primary color wavelength bands different from each other, and a narrow-band filter that has a wavelength band narrower than a wavelength band where each of the plurality of wide-band filters transmits wide-band light and transmits narrow-band light included in a part of the wavelength bands of the wide-band light. In each of the filter units, the number of filters of the narrow-band filter is greater than or equal to the number of filters of any one of the plurality of wide-band filters, corresponding to a plurality of pixels.

Figure 3:
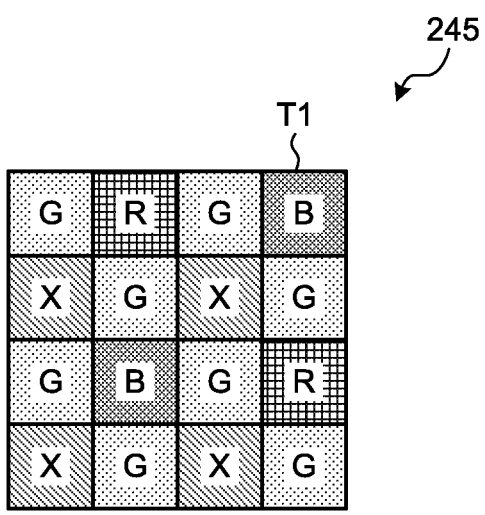
FIG. 3 is a diagram schematically illustrating a configuration of a color filter according to the first embodiment of the present disclosure.

FIG. 3 is a diagram schematically illustrating a configuration of the color filter 245. The color filter 245 illustrated in FIG. 3 is formed by, for example, arranging filter units T1, in each of which filters are arranged in a matrix form of 4×4 (16) being repeated as one pattern, in a matrix form according to an arrangement of pixels of the imaging sensor 244. A pixel where a filer is provided receives light of a wavelength band that the filter transmits. For example, a pixel where a wide-band filter G that transmits light of a green wavelength band is provided receives light of a green wavelength band. Hereinafter, a pixel that receives light of a green wavelength band is referred to as a G pixel. In the same manner, a pixel that receives light of a blue wavelength band is referred to as a B pixel, a pixel that receives light of a red wavelength band is referred to as an R pixel, and a pixel that receives narrow-band light is referred to as an X pixel.

The filter unit T1 illustrated in FIG. 3 includes two wide-band filters R that transmit light of a red wavelength band (620 nm to 750 nm), eight wide-band filters G that transmit light of a green wavelength band (495 nm to 570 nm), two wide-band filters B that transmit light of a blue wavelength band (450 nm to 495 nm), and four narrow-band filters X that transmit a part of light of the blue wavelength band and transmit narrow-band light having a wavelength band narrower than a wavelength band that each wide-band filter transmits, as one pattern. The pattern is repeatedly arranged. In the filter unit T1, the number of narrow-band filters X is greater than the number of wide-band filters B (4>2). In the filter unit T1, the number of wide-band filters G is eight, which is the same as in the Bayer array, in order to maintain the resolution of a white image, and the number of narrow-band filters X is four in order to increase the resolution of a narrow-band image. In the filter unit T1, the wide-band filter B and the narrow-band filter X are highly correlated with each other, so that the number of wide-band filters B is two. The number of wide-band filters R is two because there is not so much red in the large intestine.

Figure 4:
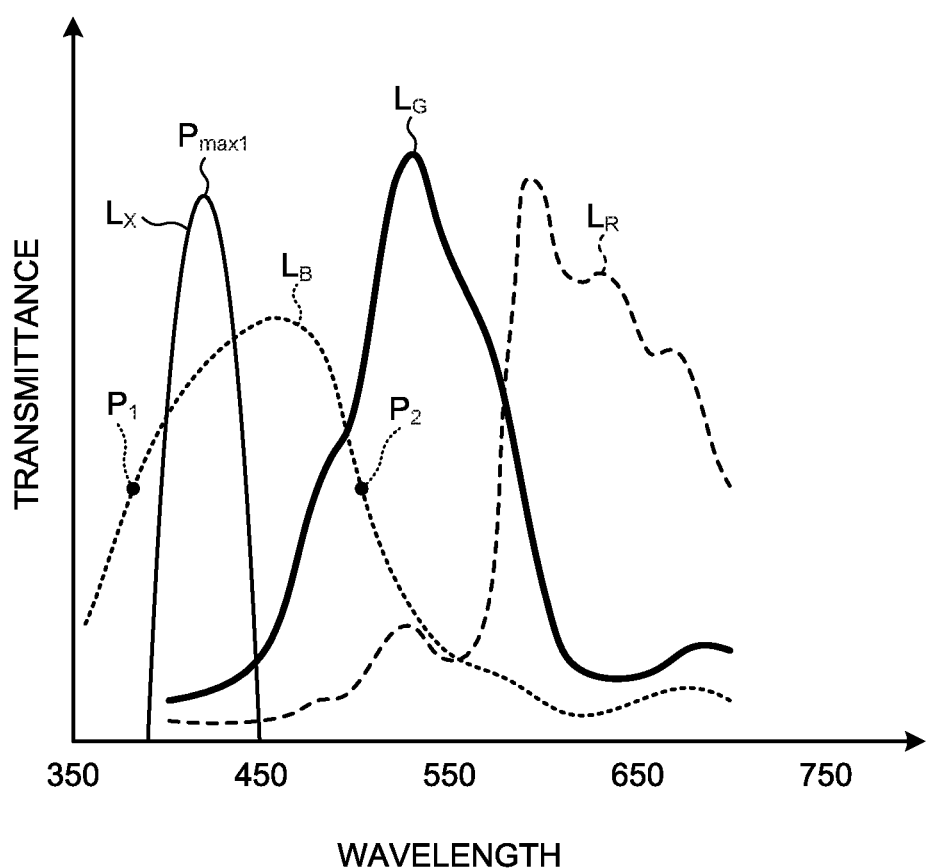
FIG. 4 is a diagram illustrating transmittance characteristics of each filter included in the color filter according to the first embodiment of the present disclosure.

FIG. 4 is a diagram illustrating transmittance characteristics of each filter included in the color filter 245. In FIG. 4, the horizontal axis indicates the wavelength and the vertical axis indicates the transmittance. In FIG. 4, the curved line $L_B$ indicates the transmittance characteristics of the wide-band filter B, the curved line $L_G$ indicates the transmittance characteristics of the wide-band filter G, the curved line $L_R$ indicates the transmittance characteristics of the wide-band filter R, and the curved line $L_X$ indicates the transmittance characteristics of the narrow-band filter X. Further, in FIG. 4, it is assumed that the peak wavelength of the narrow-band filter X is 415 nm±30 nm.

As indicated by the curved line $L_X$ in FIG. 4, the narrow-band filter X has a wavelength band narrower than that of the wide-band light transmitted by the wide-band filter B and has a transmission spectrum that transmits narrow-band light included in a part of the wavelength band transmitted by the wide-band filter B. Further, as illustrated in the curved line $L_X$ in FIG. 4, the wavelength band of light that passes through the wide-band filter B and the wavelength band of light that passes through the narrow-band filter X are highly correlated with each other. Specifically, as illustrated by the curved line $L_X$ and the curved line $L_B$, the maximum value $P_{max1}$ of the transmission spectrum of the narrow-band filter X is included in a half value width between the lower limit value $P_1$ that is one-half the maximum value of the transmission spectrum of the wide-band filter B and the upper limit value $P_2$. Further, as illustrated by the curved line $L_G$ and the curved line $L_R$, an optical spectrum of the wide-band filter G and an optical spectrum of the wide-band filter R overlap with each other, so that they are highly correlated with each other.

Let us return to FIGS. 1 and 2. The description of the endoscope 2 will be continued.

The AFE unit 246 reduces a noise component included in an image signal input from the imaging sensor 244, performs CDS (Correlated Double Sampling) processing that adjusts an amplification factor of the image signal to maintain a constant output level and A/D conversion processing that A/D converts the image signal, and outputs the image signal to the processing device 4.

The TG unit 247 generates pulses of various signal processing operations for driving each of the imaging sensor 244 and the imaging controller 248. The TG unit 247 outputs a pulse signal to the imaging sensor 244 and the imaging controller 248.

The imaging controller 248 controls imaging of the imaging sensor 244. The imaging controller 248 is formed of a CPU (Central Processing Unit), registers that record various programs, and the like.

The operating unit 22 includes a bending knob 221 that bends the bending portion 25 in a vertical direction and a horizontal direction, a treatment tool insertion unit 222 through which treatment tools such as biopsy forceps, an electric scalpel, and an inspection probe are inserted into a body cavity of the subject, and a plurality of switches 223 which is an operation input unit from which an operation instruction signal for peripheral apparatuses such as an air supply unit, a water supply unit, and a screen display control in addition to the processing device 4 and the light source device 3 is input. The treatment tool inserted from the treatment tool insertion unit 222 is exposed from an opening portion (not illustrated in the drawings) through a treatment tool channel (not illustrated in the drawings) of the distal end portion 24.

The universal cord 23 incorporates at least the light guide 241 and one or a plurality of signal lines. The universal cord 23 includes at least a signal for transmitting a clock signal and a synchronization signal output from the processing device 4 described later.

Configuration of Light Source Device

Next, a configuration of the light source device 3 will be described. The light source device 3 includes an illumination unit 31 and an illumination controller 32.

The illumination unit 31 emits a plurality of illumination lights respectively having different wavelength bands to the object (subject) by sequentially switching the plurality of illumination lights under control of the illumination controller 32. The illumination unit 31 includes a light source unit 311 and a light source driver 312.

The light source unit 311 includes a light source such as a xenon lamp or a white LED (Light Emitting Diode), one or a plurality of lenses, and the like. The light source unit 311 emits white light under control of the light source driver 312. The light source unit 311 may include a red LED, a green LED, and a blue LED, and emit white light to the object by causing the red LED, the green LED, and the blue LED to emit light simultaneously.

The light source driver 312 causes the light source unit 311 to emit white light by supplying an electric current to the light source unit 311 under control of the illumination controller 32.

The illumination controller 32 causes the light source unit 311 to emit white light at a predetermined cycle under control of the processing device 4.

Configuration of Processing Device

Next, a configuration of the processing device 4 will be described. The processing device 4 includes an image processing unit 401, a brightness detection unit 402, a light control unit 403, an input unit 404, a recording unit 405, a reference clock generation unit 406, a synchronization signal generation unit 407, and a control unit 408.

Image processing unit 401 generates an in-vivo image to be displayed by the display device 5 based on an image signal input from the endoscope 2 and outputs the in-vivo image to the display device 5. The image processing unit 401 generates an in-vivo image by performing predetermined image processing on the image signal.

Here, a detailed configuration of the image processing unit 401 will be described. The image processing unit 401 includes at least a separation unit 401a, a demosaicing unit 401b, and an image generation unit 401c.

The separation unit 401a separates a plurality of wide-band image signals corresponding to wide-band light having passed through each of a plurality of wide-band filters and a plurality of narrow-band image signals corresponding to narrow-band light having passed through each of a plurality of narrow-band filters, from each other, based on the image signal input from the endoscope 2. Specifically, the separation unit 401a separates the image signal (RAW data) input from the endoscope 2 into a wide-band image signal corresponding to wide-band light having passed through the wide-band filter R, a wide-band image signal corresponding to wide-band light having passed through the wide-band filter G, a wide-band image signal corresponding to wide-band light having passed through the wide-band filter B, and a narrow-band image signal corresponding to narrow-band light having passed through the narrow-band filter X.

The demosaicing unit 401b performs demosaic processing that interpolates any one of a plurality of wide-band image signals based on the narrow-band image signal separated by the separation unit 401a. Specifically, the demosaicing unit 401b performs demosaic processing that interpolates the wide-band image signal corresponding to wide-band light having passed through the wide-band filter B based on the narrow-band image signal separated by the separation unit 401a. Further, the demosaicing unit 401b performs demosaic processing that interpolates an image signal of R pixel by using an image signal of G pixel.

The image generation unit 401c generates a wide-band image by using the wide-band image signal interpolated by the demosaic processing performed by the demosaicing unit 401b and generates a narrow-band image by using the narrow-band image signal. Specifically, the image generation unit 401c generates a color normal image based on an RGB image signal made into the Bayer array by the demosaicing unit 401b. Further, the image generation unit 401c generates a narrow-band image by interpolating an image signal of a missing pixel by performing demosaic processing based on an image signal of an X pixel.

The brightness detection unit 402 detects a brightness level corresponding to each pixel based on RGB image information from an image signal input from the image processing unit 401, records the detected brightness level into a memory provided inside the brightness detection unit 402, and outputs the detected brightness level to the control unit 408.

The light control unit 403 sets a light emitting condition such as the amount of light emitted by the light source device 3 and a light emitting timing based on the brightness level detected by the brightness detection unit 402 and outputs a light control signal including the set light emitting condition to the light source device 3 under control of the control unit 408.

The input unit 404 receives inputs of various signals such as an operation instruction signal that instructs an operation of the endoscope system 1. The input unit 404 includes switches and the like.

The recording unit 405 records various programs to cause the endoscope system 1 to operate and data including various parameters necessary for the operation of the endoscope system 1. Further, the recording unit 405 records identification information of the processing device 4. Here, the identification information includes unique information (ID), model year, specification information, transmission method, and transmission rate of the processing device 4.

The reference clock generation unit 406 generates a clock signal to be a reference of operation of each component of the endoscope system 1 and supplies the generated clock signal to each component of the endoscope system 1. In the first embodiment, the reference clock generation unit 406 functions as a clock signal generation unit.

The synchronization signal generation unit 407 generates a synchronization signal based on the clock signal input from the reference clock generation unit 406 and outputs the synchronization signal to the TG unit 247 of the endoscope 2 and the image processing unit 401.

The control unit 408 performs drive control of each component including the imaging sensor 244 and the light source device 3 and input/output control of information to and from each component. The control unit 408 includes a CPU.

Configuration of Display Device

Next, the display device 5 will be described. The display device 5 displays an in-vivo image corresponding to an image signal input from the processing device 4 through an image cable. The display device 5 is configured by using a liquid crystal or, an organic EL (Electro Luminescence), or the like.

Processing of Image Processing Unit

Figure 5:
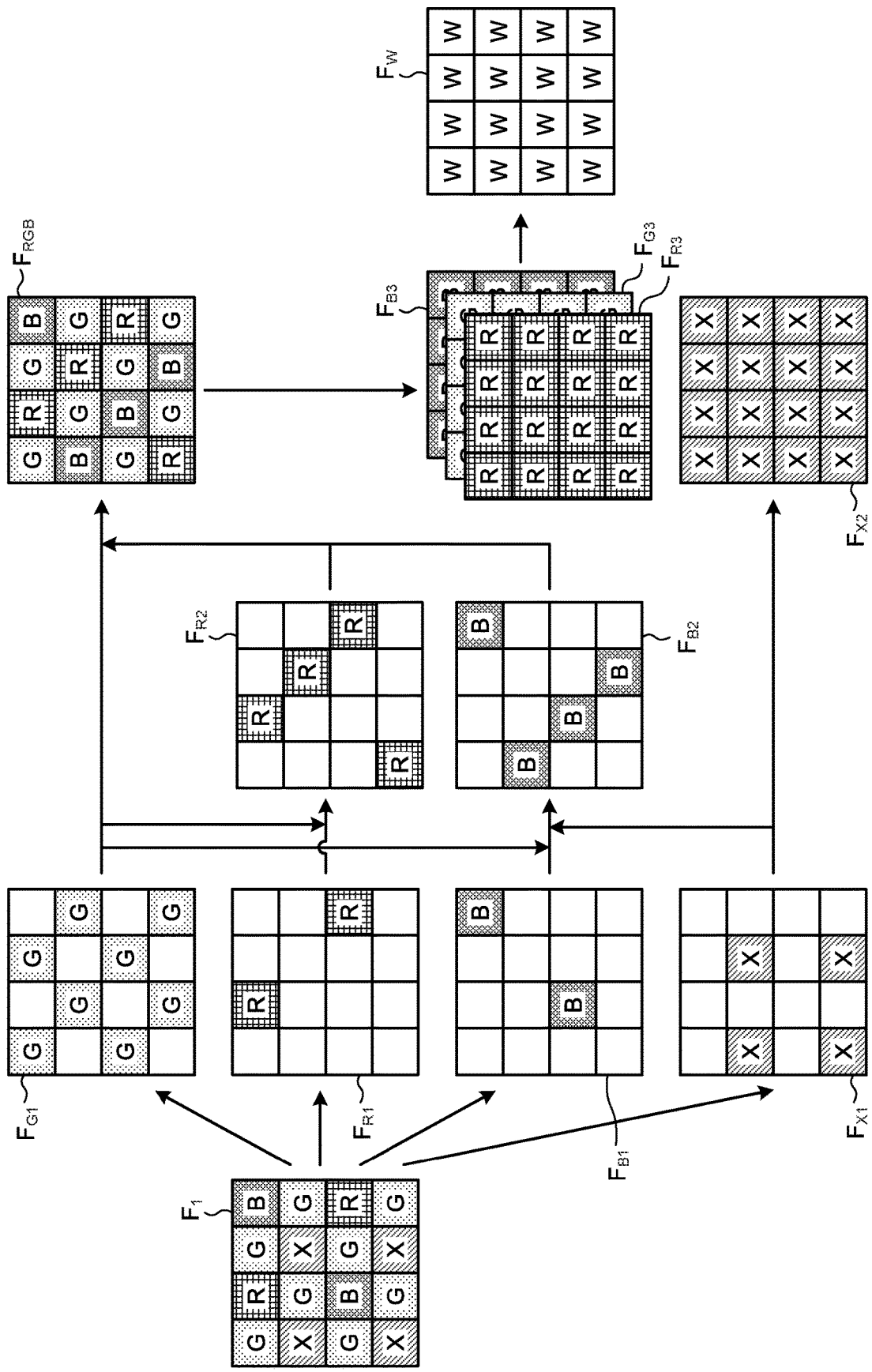
FIG. 5 is a diagram for schematically explaining an overview of image processing performed by an image processing unit according to the first embodiment of the present disclosure.

Next, the image processing performed by the image processing unit 401 will be described. FIG. 5 is a diagram for schematically explaining an overview of the image processing performed by the image processing unit 401.

As illustrated in FIG. 5, first, the separation unit 401a separates RAW data $F_1$ input from the imaging sensor 244 of the endoscope 2 into image signals of each pixel. Specifically, the separation unit 401a separates the RAW data $F_1$ into image data so that wide-band image signals corresponding to G pixels become image data $F_{G1}$ of the Bayer array, wide-band image signals corresponding to R pixels become image data $F_{R1}$, wide-band image signals corresponding to B pixels become image data $F_{B1}$, and narrow-band image signals corresponding to X pixels become image data $F_{X1}$.

As illustrated in FIG. 5, in the image data $F_{R1}$, the number of wide-band image signals from R pixels corresponding to the wide-band filter R is smaller than that of the Bayer array. Further, the transmission spectrum (spectral characteristics) of the wide-band filter G and the transmission spectrum (spectral characteristics) of the wide-band filter R overlap with each other and they are highly correlated with each other (see FIG. 4). Therefore, the demosaicing unit 401b generates image data $F_{R2}$ of the Bayer array by interpolating the wide-band image signals of R pixels that are missing by the demosaic processing based on the wide-band image signals of the image data $F_{G1}$.

In the image data $F_{B1}$, the number of wide-band image signals from B pixels corresponding to the wide-band filter B is smaller than that of the Bayer array. Further, although deep and superficial blood vessels are imaged, edge information is blurred because the image data $F_{B1}$ is wide-band, so that the resolution is lowered. The spectral characteristics of the wide-band filter B includes the spectral characteristics of the narrow-band filter X and the transmission spectrum of the wide-band filter G and the transmission spectrum of the narrow-band filter X overlap with each other and have high correlation with each other (see FIG. 4). Therefore, the demosaicing unit 401b generates image data $F_{B2}$ of the Bayer array by interpolating the wide-band image signals of B pixels that are missing by the demosaic processing based on the wide-band image signals of the image data $F_{G1}$ and the narrow-band image signals of the image data $F_{X1}$. In this case, when there are the wide-band image signals of the image data $F_{G1}$ and the narrow-band image signals of the image data $F_{X1}$ with respect to the missing B pixels, to more clearly detect superficial blood vessels of a gastrointestinal mucosal membrane, the demosaicing unit 401b interpolates the wide-band image signals of the missing B pixels by the demosaic processing by preferentially using the narrow-band image signals of the image data $F_{X1}$ because the narrow-band image signals include much more detailed edge information. Thereby, RAW data $F_{RGB}$ of a conventional Bayer array may be obtained, and the image data $F_{B1}$ may be obtained with high resolution.

Subsequently, the demosaicing unit 401b generates image data $F_{R3}$, image data $F_{G3}$, and image data $F_{B3}$ of RGB, respectively, by performing Bayer demosaic processing based on the RAW data $F_{RGB}$ of the Bayer array.

Thereafter, the image generation unit 401c generates color normal image data $F_W$ (white image) based on the image data $F_{R3}$, the image data $F_{G3}$, and the image data $F_{B3}$ of RGB, respectively, which are generated by the demosaicing unit 401b, and outputs the color normal image data $F_W$ to the display device 5.

Further, the image generation unit 401c generates narrow-band image data $F_{X2}$ by interpolating the missing X pixels by performing demosaic processing based on the image signals of the image data $F_{X1}$ and outputs the narrow-band image data $F_{X2}$ to the display device 5.

According to the first embodiment of the present disclosure described above, the demosaicing unit 401b performs the demosaic processing that interpolates the wide-band image signals corresponding to the wide-band filter B based on the narrow-band image signals corresponding to the narrow-band light having passed through the narrow-band filter X. Thereby, a wide-band image and a narrow-band image may be obtained at high resolutions, respectively.

Modified Example of First Embodiment

Next, a modified example of the first embodiment of the present disclosure will be described. A configuration of a color filter 245 of an endoscope system according to the modified example of the first embodiment is different from that of the endoscope system 1 according to the first embodiment described above. Therefore, in the description below, only the configuration of the color filter according to the modified example of the first embodiment will be described. The same components as those of the endoscope system 1 according to the first embodiment described above are denoted by the same reference symbols and the descriptions thereof will be omitted.

Figure 6:
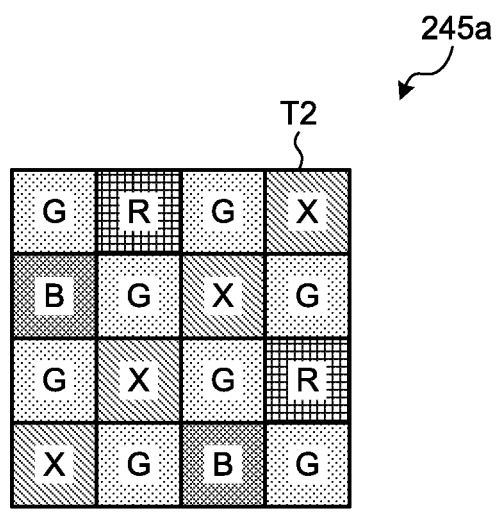
FIG. 6 is a diagram schematically illustrating a configuration of a color filter according to a modified example of the first embodiment of the present disclosure.

FIG. 6 is a diagram schematically illustrating the configuration of the color filter according to the modified example of the first embodiment of the present disclosure.

A color filter 245a illustrated in FIG. 6 is provided by being laminated on a light receiving surface of the imaging sensor 244. The color filter 245a is formed by, for example, arranging filter units T2, in each of which filters are arranged in a matrix form of 4×4 (16) being repeated as one pattern, in a matrix form according to an arrangement of pixels of the imaging sensor 244. The color filter 245a is formed by arranging the filter units T2. Each of the filter units T2 is formed by using a plurality of wide-band filters that transmits wide-band light including primary color wavelength bands different from each other, and a narrow-band filter that has a wavelength band narrower than a wavelength band where each of the plurality of wide-band filters transmits wide-band light and transmits narrow-band light included in a part of the wavelength bands of the wide-band light. In each of the filter units T2, the number of filters of the narrow-band filter is greater than or equal to the number of filters of any one of the plurality of wide-band filters, corresponding to a plurality of pixels.

The filter unit T2 illustrated in FIG. 6 includes two wide-band filters R that transmit a red color component, eight wide-band filters G that transmit a green red color component, two wide-band filters B that transmit a blue color component, and four narrow-band filters X that have a wavelength band narrower than that of the light passing through the wide-band filter B and transmit narrow-band light included in a part of the wavelength band transmitted by the wide-band filter B, as one pattern. The pattern is repeatedly arranged. In the filter unit T2, the number of wide-band filters G is eight, which is the same as in the Bayer array, in order to maintain the resolution of a white image, and the number of narrow-band filters X is four in order to increase the resolution of a narrow-band image. In the filter unit T2, the wide-band filter B and the narrow-band filter X are highly correlated with each other, so that the number of wide-band filters B is two. The number of wide-band filters R is two because there is not so much red in the large intestine.

According to the modified example of the first embodiment described above, the same effect as that of the first embodiment described above is obtained.

Second Embodiment

Next, a second embodiment of the present disclosure will be described. A configuration of a color filter and processing of an image processing unit of an endoscope system according to the second embodiment are different from those of the endoscope system 1 according to the first embodiment described above. Therefore, in the description below, the configuration of the color filter according to the second embodiment will be described, and thereafter the processing performed by the image processing unit according to the second embodiment will be described. The same components as those of the endoscope system 1 according to the first embodiment described above are denoted by the same reference symbols and the descriptions thereof will be omitted.

Configuration of Color Filter

Figure 7:
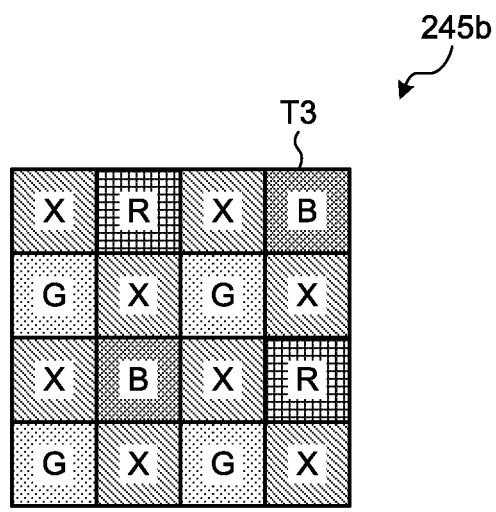
FIG. 7 is a diagram schematically illustrating a configuration of a color filter according to a second embodiment of the present disclosure.

FIG. 7 is a diagram schematically illustrating the configuration of the color filter according to the second embodiment. A color filter 245b illustrated in FIG. 7 is formed by, for example, arranging filter units T3, in each of which filters are arranged in a matrix form of 4×4 (16) being repeated as one pattern, in a matrix form according to an arrangement of pixels of the imaging sensor 244. The color filter 245b is formed by arranging the filter units T3. Each of the filter units T3 is formed by using a plurality of wide-band filters that transmits wide-band light including primary color wavelength bands different from each other, and a narrow-band filter that has a wavelength band narrower than a wavelength band where each of the plurality of wide-band filters transmits wide-band light and transmits narrow-band light included in a part of the wavelength bands of the wide-band light. In each of the filter units T3, the number of filters of the narrow-band filter is greater than or equal to the number of filters of any one of the plurality of wide-band filters, corresponding to a plurality of pixels.

Specifically, as illustrated in FIG. 7, the filter unit T3 includes two wide-band filters R that transmit light of a red wavelength band, four wide-band filters G that transmit light of a green wavelength band, two wide-band filters B that transmit light of a blue wavelength band, and eight narrow-band filters X that have a wavelength band narrower than that of the light passing through a wide-band filter and transmit narrow-band light included in a part of the wavelength band transmitted by a wide-band filter, as one pattern. The pattern is repeatedly arranged.

Figure 8:
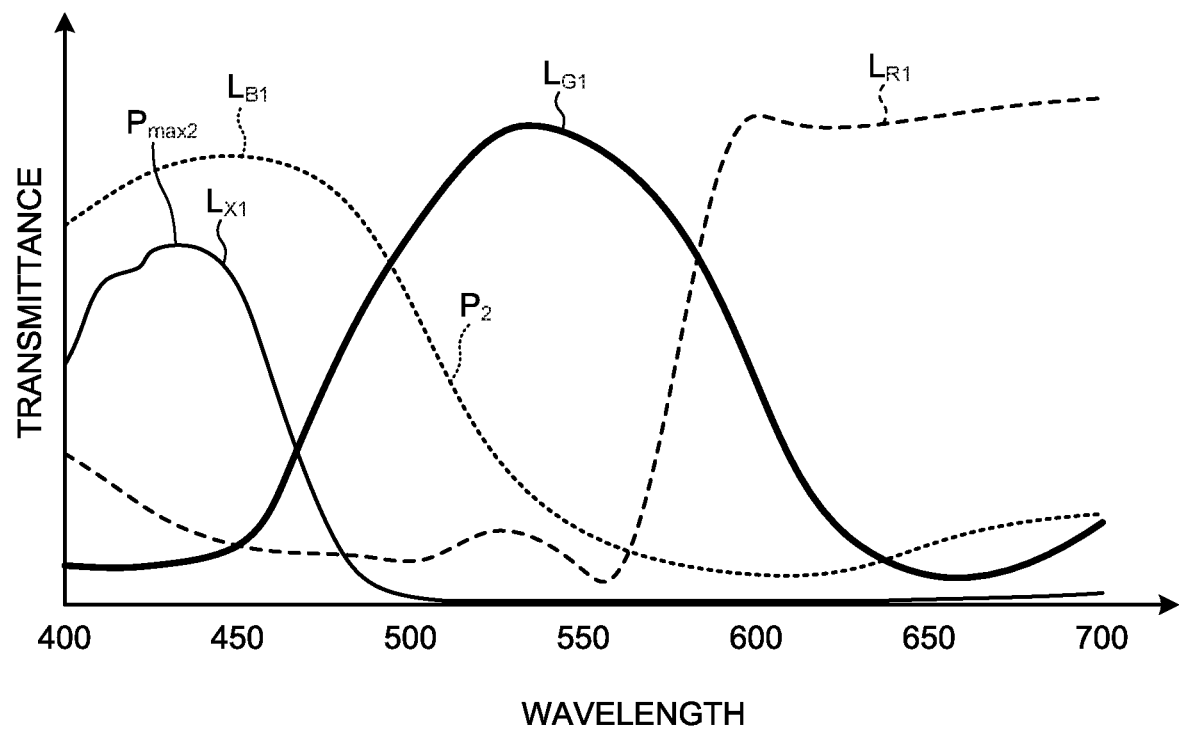
FIG. 8 is a diagram illustrating transmittance characteristics of each filter included in the color filter according to the second embodiment of the present disclosure.

FIG. 8 is a diagram illustrating transmittance characteristics of each filter included in the color filter 245b. In FIG. 8, the horizontal axis indicates the wavelength and the vertical axis indicates the transmittance. In FIG. 8, the curved line $L_{B1}$ indicates the transmittance characteristics of the wide-band filter B, the curved line $L_{G1}$ indicates the transmittance characteristics of the wide-band filter G, the curved line $L_{R1}$ indicates the transmittance characteristics of the wide-band filter R, and the curved line $L_{X1}$ indicates the transmittance characteristics of the narrow-band filter X. Further, in FIG. 8, it is assumed that the peak wavelength of the narrow-band filter X is 415 nm±30 nm.

As indicated by the curved line $L_{X1}$ and the curved line $L_{B1}$ in FIG. 8, the narrow-band filter X has a wavelength band narrower than that of the wide-band light transmitted by the wide-band filter B and has a transmission spectrum that transmits narrow-band light included in a part of the wavelength band transmitted by the wide-band filter B. Further, the wavelength band transmitted by the wide-band filter B and the wavelength band transmitted by the narrow-band filter X are highly correlated with each other. Furthermore, the maximum value $P_{max2}$ of the transmission spectrum, where light transmits, of the narrow-band filter X is included in a half value width between the lower limit value and the upper limit value $P_2$ of the transmission spectrum of light that passes through the wide-band filter B. Further, as illustrated by the curved line $L_{G1}$ and the curved line $L_{R1}$, the transmission spectrum of the wide-band filter G and the transmission spectrum of the wide-band filter R overlap with each other, so that they are highly correlated with each other.

Processing of Image Processing Unit

Figure 9:
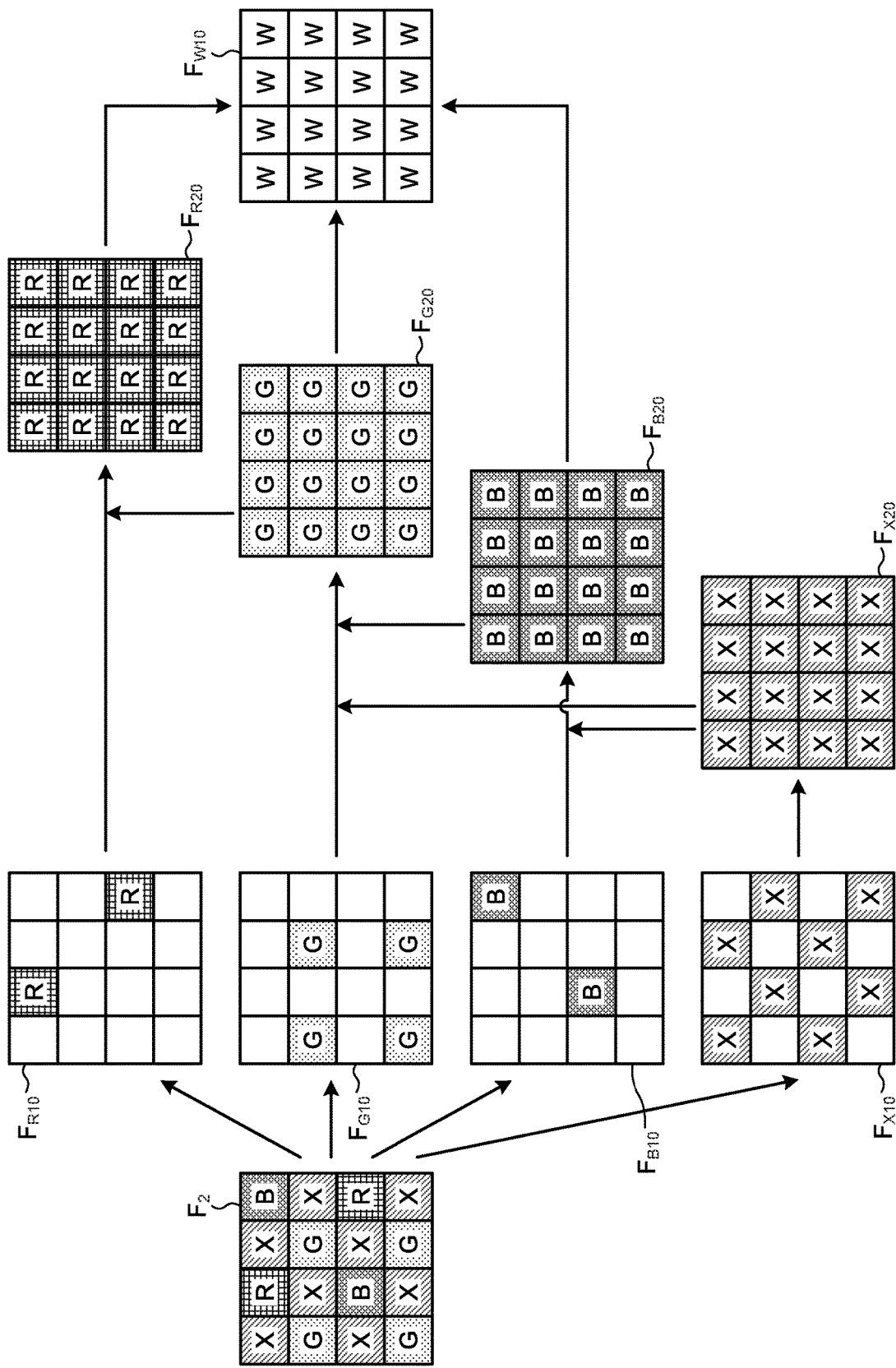
FIG. 9 is a diagram for schematically explaining an overview of image processing performed by an image processing unit according to the second embodiment of the present disclosure.

Next, the processing performed by the image processing unit 401 will be described. FIG. 9 is a diagram for schematically explaining an overview of the image processing performed by the image processing unit 401.

As illustrated in FIG. 9, first, the separation unit 401a separates RAW data $F_2$ input from the imaging sensor 244 of the endoscope 2 into image signals of each pixel. Specifically, the separation unit 401a separates the RAW data $F_2$ into image data so that wide-band image signals corresponding to G pixels become image data $F_{G10}$ of the Bayer array, wide-band image signals corresponding to R pixels become image data $F_{R10}$, wide-band image signals corresponding to B pixels become image data $F_{B10}$, and narrow-band image signals corresponding to X pixels become image data $F_{X10}$.

Next, the image generation unit 401c generates narrow-band image data $F_{X20}$ by interpolating narrow-band image signals by performing demosaic processing on the missing X pixels based on the narrow-band image signals of the image data $F_{X10}$, and outputs the narrow-band image data $F_{X20}$ to the display device 5.

In the narrow-band image data $F_{X20}$, detailed edge information of capillary vessels is included in the narrow-band image signals. Therefore, the demosaicing unit 401b generates wide-band image data $F_{B20}$ by interpolating the wide-band image signals of B pixels missing in the image data $F_{B10}$ by performing demosaic processing based on the narrow-band image signals of the narrow-band image data $F_{X20}$.

Thereafter, the demosaicing unit 401b generates wide-band image data $F_{G20}$ by interpolating the wide-band image signals of G pixels missing in the image data $F_{G10}$ by performing demosaic processing based on the edge information from the narrow-band image signals of the narrow-band image data $F_{X20}$ and the wide-band image data $F_{B20}$.

Subsequently, the demosaicing unit 401b generates wide-band image data $F_{R20}$ by interpolating the wide-band image signals of R pixels missing in the image data $F_{R10}$ by performing demosaic processing based on the wide-band image signals of the wide-band image data $F_{G20}$.

Thereafter, the image generation unit 401c generates color normal image data $F_{W10}$ (white image) based on the wide-band image data $F_{R20}$, the wide-band image data $F_{G20}$, and the wide-band image data $F_{B20}$ of RGB, respectively, which are generated by the demosaicing unit 401b, and outputs the color normal image data $F_{W10}$ to the display device 5.

According to the second embodiment of the present disclosure described above, the demosaicing unit 401b interpolates the wide-band image signals of B pixels by performing demosaic processing by using the narrow-band image signals output by the X pixels. Thereby, a normal image and a narrow-band image may be obtained at high resolutions, respectively.

Third Embodiment

Next, a third embodiment of the present disclosure will be described. A configuration of a color filter and processing of an image processing unit of an endoscope system according to the third embodiment are different from those of the endoscope system 1 according to the first embodiment described above. Specifically, the color filter according to the third embodiment has two types of narrow-band filters whose transmission spectra are different from each other. Therefore, in the description below, the configuration of the color filter according to the third embodiment will be described, and thereafter the processing performed by the image processing unit according to the third embodiment will be described. The same components as those of the endoscope system 1 according to the first embodiment described above are denoted by the same reference symbols and the descriptions thereof will be omitted.

Configuration of Color Filter

Figure 10:
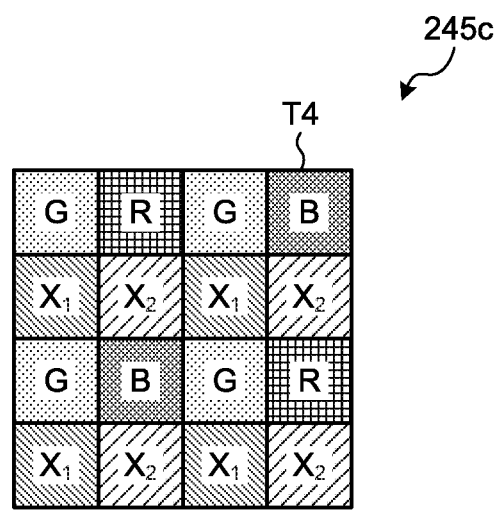
FIG. 10 is a diagram schematically illustrating a configuration of a color filter according to a third embodiment of the present disclosure.

FIG. 10 is a diagram schematically illustrating the configuration of the color filter according to the third embodiment. A color filter 245c illustrated in FIG. 10 is formed by, for example, arranging filter units T4, in each of which filters are arranged in a matrix form of 4×4 (16) being repeated as one pattern, in a matrix form according to an arrangement of pixels of the imaging sensor 244. The color filter 245c is formed by arranging the filter units T4. Each of the filter units T4 is formed by using a plurality of wide-band filters that transmits wide-band light including primary color wavelength bands different from each other, and a narrow-band filter that has a wavelength band narrower than a wavelength band where each of the plurality of wide-band filters transmits wide-band light and transmits narrow-band light included in a part of the wavelength bands of the wide-band light. In each of the filter units T4 the number of filters of the narrow-band filter is greater than or equal to the number of filters of any one of the plurality of wide-band filters, corresponding to a plurality of pixels.

The filter unit T4 illustrated in FIG. 10 includes two wide-band filters R that transmit light of a red wavelength band, four wide-band filters G that transmit light of a green wavelength band, two wide-band filters B that transmit light of a blue wavelength band, four narrow-band filters $X_1$ that have a wavelength band narrower than that of the light passing through the wide-band filter B and transmit narrow-band light included in a part of the wavelength band transmitted by the wide-band filter B, and four narrow-band filters $X_2$ that have a wavelength band narrower than that of the light passing through the wide-band filter G and transmit narrow-band light included in a part of the wavelength band transmitted by the wide-band filter G, as one pattern. The pattern is repeatedly arranged.

Figure 11:
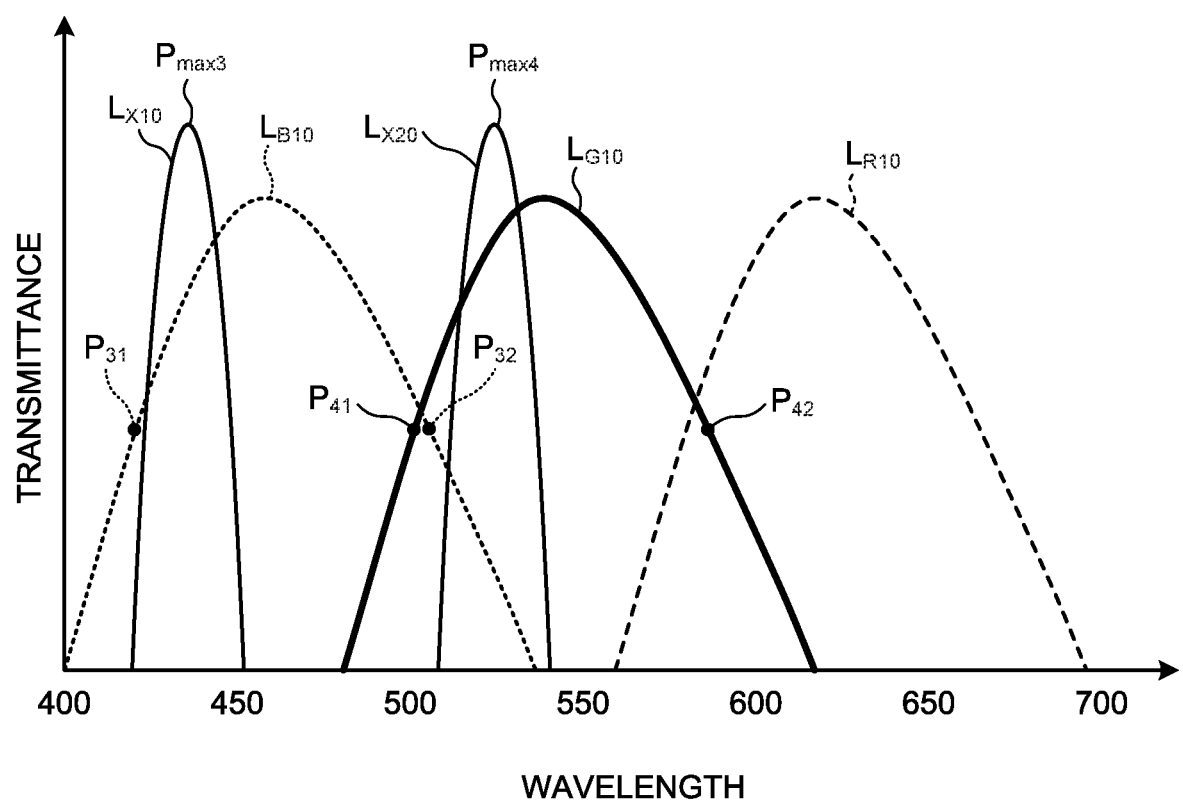
FIG. 11 is a diagram illustrating transmittance characteristics of each filter included in the color filter according to the third embodiment of the present disclosure.

FIG. 11 is a diagram illustrating transmittance characteristics of each filter included in the color filter 245c. In FIG. 11, the horizontal axis indicates the wavelength and the vertical axis indicates the transmittance. In FIG. 11, the curved line $L_{B10}$ indicates the transmittance characteristics of the wide-band filter B, the curved line $L_{G10}$ indicates the transmittance characteristics of the wide-band filter G, the curved line $L_{R10}$ indicates the transmittance characteristics of the wide-band filter R, the curved line $L_{X10}$ indicates the transmittance characteristics of the narrow-band filter $X_1$, and the curved line $L_{X20}$ indicates the transmittance characteristics of the narrow-band filter $X_2$. Further, in FIG. 11, it is assumed that the peak wavelength of the narrow-band filter $X_1$ is 415 nm±30 nm and the peak wavelength of the narrow-band filter $X_2$ is 540 nm±30 nm.

As indicated by the curved line $L_{X10}$ and the curved line $L_{B10}$ in FIG. 11, the narrow-band filter $X_1$ has a wavelength band narrower than the wavelength band transmitted by the wide-band filter B and has a transmission spectrum that transmits narrow-band light included in a part of the wavelength band transmitted by the wide-band filter B. Further, as indicated by the curved line $L_{X10}$ and the curved line $L_{B10}$, the transmission spectrum transmitted by the wide-band filter B and the transmission spectrum transmitted by the narrow-band filter $X_1$ are highly correlated with each other. Furthermore, as indicated by the curved line $L_{X10}$ and the curved line $L_{B10}$, the maximum value $P_{max3}$ of the transmission spectrum, where light transmits, of the narrow-band filter $X_1$ is included in a half value width between the lower limit value $P_{31}$ and the upper limit value $P_{32}$ of the transmission spectrum of light that passes through the wide-band filter B.

As indicated by the curved line $L_{X20}$ and the curved line $L_{G10}$ in FIG. 11, the narrow-band filter $X_2$ has a wavelength band narrower than the wavelength band where the wide-band filter G transmits light and has a transmission spectrum that transmits narrow-band light included in a part of the wavelength band where the wide-band filter G transmits light. Further, as indicated by the curved line $L_{X20}$ and the curved line $L_{G10}$, the transmission spectrum transmitted by the wide-band filter G and the transmission spectrum transmitted by the narrow-band filter $X_2$ are highly correlated with each other. Furthermore, as indicated by the curved line $L_{X20}$ and the curved line $L_{G10}$, the maximum value $P_{max4}$ of the transmission spectrum, where light transmits, of the narrow-band filter $X_2$ is included in a half value width between the lower limit value $P_{41}$ and the upper limit value $P_{42}$ of the transmission spectrum of light that passes through the wide-band filter G.

Processing of Image Processing Unit

Figure 12:
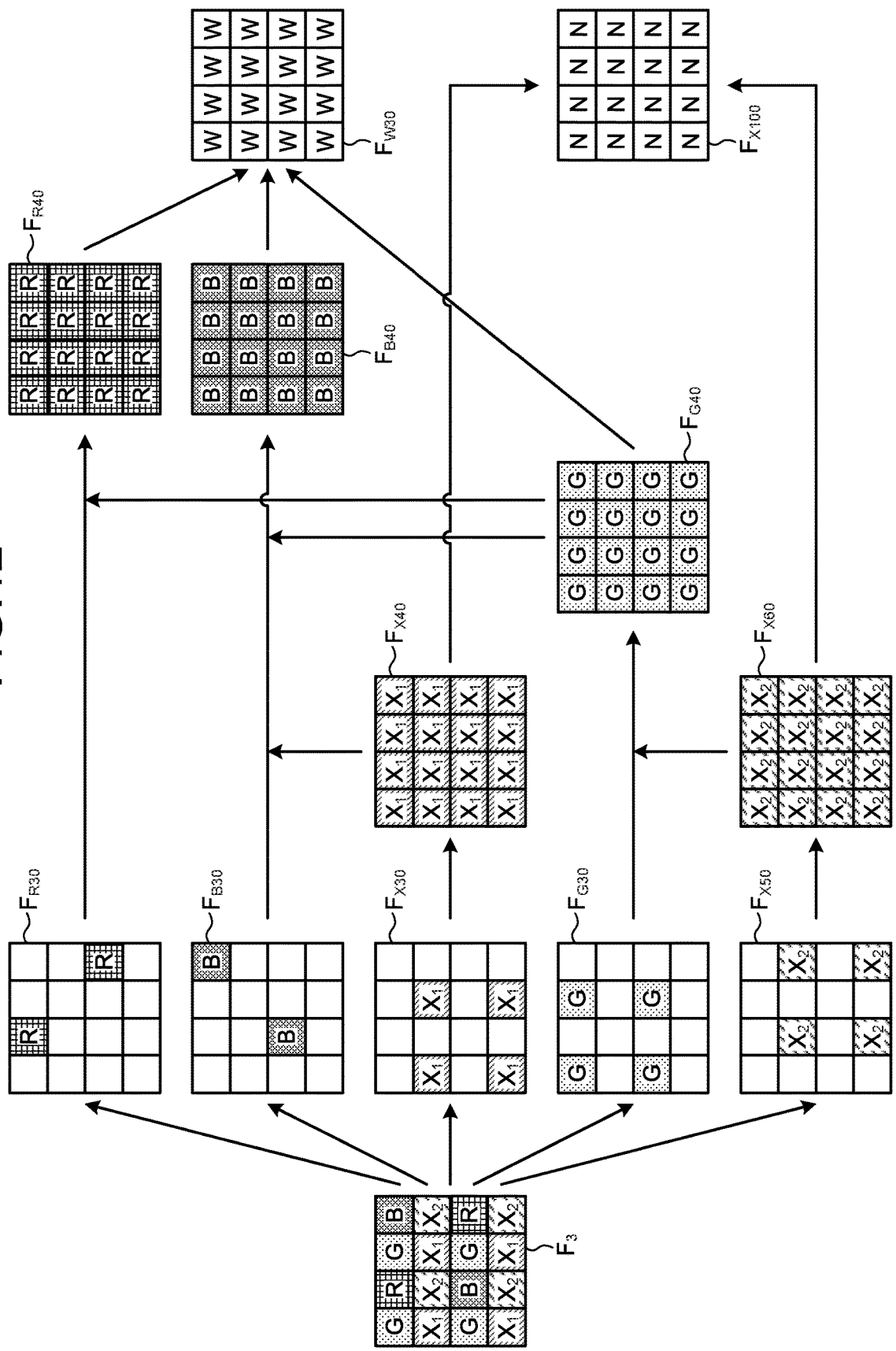
FIG. 12 is a diagram for schematically explaining an overview of image processing performed by an image processing unit according to the third embodiment of the present disclosure.

Next, the processing performed by the image processing unit 401 will be described. FIG. 12 is a diagram for schematically explaining an overview of the image processing performed by the image processing unit 401.

As illustrated in FIG. 12, first, the separation unit 401a separates RAW data $F_3$ input from the imaging sensor 244 of the endoscope 2 into image signals of each pixel. Specifically, the separation unit 401a separates the RAW data $F_3$ into image data so that wide-band image signals corresponding to R pixels become image data $F_{R30}$, wide-band image signals corresponding to B pixels become image data $F_{B30}$, narrow-band image signals corresponding to $X_1$ pixels become image data $F_{X30}$, wide-band image signals corresponding to G pixels become image data $F_{G30}$ of the Bayer array, and narrow-band image signals corresponding to $X_2$ pixels become image data $F_{X50}$.

Subsequently, the demosaicing unit 401b generates narrow-band image data $F_{X40}$ by interpolating the narrow-band image signals of $X_1$ pixels by performing demosaic processing on the missing $X_1$ pixels based on the image data $F_{X30}$. Further, the demosaicing unit 401b generates narrow-band image data $F_{X60}$ by interpolating the narrow-band image signals of $X_2$ pixels by performing demosaic processing on the missing $X_2$ pixels based on the image data $F_{X50}$.

The image data $F_{G30}$ is wide-band, so that it is not possible to sharply image deep blood vessels. The spectral characteristics of the wide-band filter G includes the spectral characteristics of the narrow-band filter $X_2$ and the transmission spectrum of the wide-band filter G and the transmission spectrum of the narrow-band filter $X_2$ overlap with each other and have high correlation with each other (see FIG. 11). The narrow-band image signals of $X_2$ pixels include edge information of deep blood vessels. Therefore, the demosaicing unit 401b generates wide-band image data $F_{G40}$ by interpolating the wide-band image signals of G pixels missing in the image data $F_{G30}$ by performing demosaic processing based on the narrow-band image signals of the narrow-band image data $F_{X60}$.

The image data $F_{B30}$ is wide-band, so that it is not possible to sharply image superficial blood vessels. The spectral characteristics of the wide-band filter B includes the spectral characteristics of the narrow-band filter $X_1$ and the transmission spectrum of the wide-band filter B and the transmission spectrum of the narrow-band filter $X_1$ overlap with each other and have high correlation with each other (see FIG. 11). The narrow-band image signals of $X_1$ pixels include edge information of superficial blood vessels. Therefore, the demosaicing unit 401b generates wide-band image data $F_{B40}$ by interpolating the image signals of B pixels missing in the image data $F_{330}$ by performing demosaic processing based on the image data $F_{X30}$, the narrow-band image data $F_{X40}$, and the wide-band image data $F_{G40}$. In this case, when there are the narrow-band image signals of the narrow-band image data $F_{X40}$ and the wide-band image signals of the wide-band image data $F_{G40}$ for the B pixels to be interpolated, the demosaicing unit 401b interpolates the wide-band image signals of the missing B pixels by the demosaic processing by preferentially using the narrow-band image signals of the narrow-band image data $F_{X40}$.

Thereafter, the demosaicing unit 401b generates wide-band image data $F_{R40}$ by interpolating the wide-band image signals of R pixels missing in the image data $F_{R30}$ by performing demosaic processing based on the image data $F_{R30}$ and the wide-band image data $F_{G40}$.

Subsequently, the image generation unit 401c generates white image data $F_{W30}$ based on the wide-band image data $F_{R40}$, the wide-band image data $F_{B40}$, and the wide-band image data $F_{G40}$ and outputs the white image data $F_{W30}$ to the display device 5. Further, the image generation unit 401c generates NBI (Narrow Band Imaging) image data $F_{X100}$ based on the narrow-band image data $F_{X40}$ and the narrow-band image data $F_{X60}$ and outputs the NBI image data $F_{X100}$ to the display device 5.

According to the third embodiment of the present disclosure described above, when imaging a living organ, it is possible to increase the resolution of superficial blood vessels by performing demosaic processing based on the edge information of the $X_1$ pixels and the B pixels rather than the G pixels.

Other Embodiments

Although the color filter is formed of primary color filters in the present disclosure, for example, complementary color filters (Cy, Mg, and Ye) that transmit light having complementary color wavelength components may be used. Further, as the color filer, a color filter (R, G, B, Or, and Cy) formed of primary color filters and filters (Or and Cy) that transmit light having wavelength components of orange and cyan may be used. Furthermore, a color filter (R, G, B, and W) formed of primary color filters and a filter (W) that transmits light having a wavelength component of white may be used.

In the present disclosure, an endoscope system including an image processing device is described as an example. However, it is also possible to apply the present disclosure to, for example, a capsule endoscope in which the image processing device and the imaging sensor of the present embodiments are provided in a capsule-shaped casing and which captures images in a body cavity of a subject by being orally introduced into the subject.

According to the present disclosure, there is an effect that a wide-band image and a narrow-band image may be obtained at high resolutions, respectively.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image processing device comprising:
a memory; and
a processor which executes a program to perform operations including:
separating a plurality of wide-band image signals corresponding to wide-band light that has passed through each of a plurality of wide-band filters and a narrow-band image signal corresponding to narrow-band light that has passed through a narrow-band filter, from each other, based on an image signal input from an imaging device, the imaging device including: an imaging sensor that generates the image signal by photoelectrically converting light received by each of a plurality of pixels arranged in a two-dimensional matrix, and a color filter formed of the plurality of wide-band filters that transmit the wide-band light including primary color wavelength bands different from each other and the narrow-band filter that transmits the narrow-band light in a wavelength band narrower than a wavelength band of the wide-band light transmitted by each of the plurality of wide-band filters, the narrow-band light being included in a part of the wavelength bands of the wide-band light, and a number of filters of the narrow-band filter being greater than or equal to a number of filters of at least one of the plurality of wide-band filters;

performing demosaic processing that interpolates one of the plurality of wide-band image signals based on edge information from the narrow-band image signal separated in the separating; and generating a wide-band image by using the wide-band image signal interpolated by the demosaic processing and generating a narrow-band image by using the narrow-band image signal.

2. The image processing device according to claim 1, wherein:

the plurality of wide-band filters includes a blue filter that transmits light of a blue wavelength band, a green filter that transmits light of a green wavelength band, and a red filter that transmits light of a red wavelength band, the narrow-band filter includes a first narrow-band filter having a transmission spectrum with a maximum value that is included in a half value width of a transmission spectrum of the blue filter, the demosaic processing interpolates a wide-band image signal corresponding to the blue filter by using edge information from a first narrow-band image signal corresponding to the narrow-band light passing through the first narrow-band filter, and a number of filters of the first narrow-band filter is greater than or equal to a number of filters of the blue filter.

3. The image processing device according to claim 2, wherein:

the narrow-band filter includes a second narrow-band filter having a transmission spectrum with a maximum value that is included in a half value width of a transmission spectrum of the green filter, and the demosaic processing interpolates a wide-band image signal corresponding to the green filter by using edge information from a second narrow-band image signal corresponding to the narrow-band light having passed through the second narrow-band filter.

4. The image processing device according to claim 2, wherein the demosaic processing interpolates a wide-band image signal corresponding to the green filter by using the edge information from the first narrow-band image signal corresponding to the narrow-band light having passed through the first narrow-band filter and the wide-band image signal corresponding to the blue filter on which the demosaic processing has been performed and which has been interpolated.

5. The image processing device according to claim 2, wherein when there are a wide-band image signal corresponding to the green filter and the first narrow-band image signal corresponding to the narrow-band light having passed through the first narrow-band filter, the demosaic processing is performed by using the edge information from the first narrow-band image signal and the wide-band image signal corresponding to the green filter, when interpolating the wide-band image signal corresponding to the blue filter.

6. The image processing device according to claim 1, wherein:

the plurality of wide-band filters include a blue filter that transmits light of a blue wavelength band, a green filter that transmits light of a green wavelength band, and a red filter that transmits light of a red wavelength band, the narrow-band filter includes a first narrow-band filter having a transmission spectrum with a maximum value that is included in a half value width of a transmission spectrum of the blue filter, and the demosaic processing interpolates a wide-band image signal corresponding to the green filter by using edge information from a first narrow-band image signal corresponding to the narrow-band light having passed through the first narrow-band filter.

7. The image processing device according to claim 6, wherein the demosaic processing is performed on a wide-band image signal corresponding to the blue filter by using the edge information from the first narrow-band image signal.

8. An endoscope system comprising:

the image processing device according to claim 1;

the imaging device including, the imaging sensor that generates the image signal by photoelectrically converting the light received by each of the plurality of pixels arranged in the two-dimensional matrix; and the color filter formed of the plurality of wide-band filters that transmit the wide-band light including the primary color wavelength bands different from each other and the narrow-band filter that has a transmits the narrow-band light in the wavelength band narrower than the wavelength band of the wide-band light transmitted by each of the plurality of wide-band filters, the narrow-band light being included in the part of the wavelength bands of the wide-band light, and the number of filters of the narrow-band filter being greater than or equal to the number of filters of at least one of the plurality of wide-band filters; and an insertion portion where the imaging device is provided at a distal end of the insertion portion and which is configured to be inserted into a subject.

9. The endoscope system according to claim 8, wherein in the color filter of the imaging device:

the plurality of wide-band filters includes a blue filter that transmits light of a blue wavelength band, a green filter that transmits light of a green wavelength band, and a red filter that transmits light of a red wavelength band, and the number of filters of the narrow-band filter is greater than or equal to a number of filters of the blue filter.

10. The endoscope system according to claim 9, wherein the number of filters of the narrow-band filter is greater than the number of filters of the blue filter.

11. The endoscope system according to claim 9, wherein the number of filters of the narrow-band filter is greater than or equal to a number of filters of the red filter.

12. The endoscope system according to claim 9, wherein the number of filters of the narrow-band filter is less than a number of filters of the green filter.

13. The endoscope system according to claim 9, wherein:

the number of filters of the narrow-band filter is greater than the number of filters of the blue filter, the number of filters of the narrow-band filter is greater than a number of filters of the red filter, and the number of filters of the narrow-band filter is less than a number of filters of the green filter.

14. The endoscope system according to claim 8, wherein in the color filter of the imaging device:
the plurality of wide-band filters includes a blue filter that transmits light of a blue wavelength band, a green filter that transmits light of a green wavelength band, and a red filter that transmits light of a red wavelength band, and
the number of filters of the narrow-band filter is greater than or equal to a number of filters of the red filter.

15. The endoscope system according to claim 14, wherein the number of filters of the narrow-band filter is greater than the number of filters of the red filter.

16. The endoscope system according to claim 8, wherein in the color filter of the imaging device:
the plurality of wide-band filters includes a blue filter that transmits light of a blue wavelength band, a green filter that transmits light of a green wavelength band, and a red filter that transmits light of a red wavelength band, and
the number of filters of the narrow-band filter is greater than or equal to a number of filters of the green filter.

17. The endoscope system according to claim 16, wherein the number of filters of the narrow-band filter is greater than the number of filters of the green filter.

18. The endoscope system according to claim 8, wherein in the color filter of the imaging device:
the plurality of wide-band filters includes a blue filter that transmits light of a blue wavelength band, a green filter that transmits light of a green wavelength band, and a red filter that transmits light of a red wavelength band,
the number of filters of the narrow-band filter is greater than a number of filters of the blue filter,
the number of filters of the narrow-band filter is greater than a number of filters of the red filter, and
the number of filters of the narrow-band filter is greater than a number of filters of the green filter.

19. An image processing method comprising:
separating a plurality of wide-band image signals corresponding to wide-band light passing that has passed through each of a plurality of wide-band filters and a narrow-band image signal corresponding to narrow-band light that has passed through a narrow-band filter, from each other, based on an image signal input from an imaging device, the imaging device including: an imaging sensor that generates the image signal by photoelectrically converting light received by each of a plurality of pixels arranged in a two-dimensional matrix, and a color filter formed of the plurality of wide-band filters that transmit the wide-band light including primary color wavelength bands different from each other and the narrow-band filter that transmits the narrow-band light in a wavelength band narrower than a wavelength band of the wide-band light transmitted by each of the plurality of wide-band filters, the narrow-band light being included in a part of the wavelength bands of the wide-band light, and a number of filters of the narrow-band filter being greater than or equal to number of filters of at least one of the plurality of wide-band filters;
performing demosaic processing that interpolates one of the plurality of wide-band image signals based on edge information from the narrow-band image signal separated in the separating; and
generating a wide-band image by using the wide-band image signal interpolated by the demosaic processing and generating a narrow-band image by using the narrow-band image signal.

20. A non-transitory computer-readable recording medium with an executable program stored thereon, the program being executable by a processor of an image processing device to control the image processing device to perform operations comprising:
separating a plurality of wide-band image signals corresponding to wide-band light that has passed through each of a plurality of wide-band filters and a narrow-band image signal corresponding to narrow-band light that has passed through a narrow-band filter, from each other, based on an image signal input from an imaging device including: an imaging sensor that generates the image signal by photoelectrically converting light received by each of a plurality of pixels arranged in a two-dimensional matrix, and a color filter formed of the plurality of wide-band filters that transmits the wide-band light including primary color wavelength bands different from each other and the narrow-band filter that transmits the narrow-band light in a wavelength band narrower than a wavelength band of the wide-band light transmitted by each of the plurality of wide-band filters, the narrow-band light being included in a part of the wavelength bands of the wide-band light, number of filters of the narrow-band filter being greater than or equal to number of filters of at least one of the plurality of wide-band filters;
performing demosaic processing that interpolates one of the plurality of wide-band image signals based on edge information from the narrow-band image signal separated in the separating; and
generating a wide-band image by using the wide-band image signal interpolated by the demosaic processing and generating a narrow-band image by using the narrow-band image signal.

* * * * *